United States Patent [19]

Ikeguchi et al.

[11] Patent Number: 4,933,354

[45] Date of Patent: Jun. 12, 1990

[54] 2-PYRROLIDONE-5-CARBOXYLIC ACID COMPOUNDS USEFUL FOR THE TREATMENT OF MENTAL DISORDERS

[75] Inventors: Seiichi Ikeguchi, Kisofukushima; Yukihiko Kinoshita, Matsumoto; Hiroshi Kaneto, Nagasaki; Yukiyoshi Ajisawa, Okaya, all of Japan

[73] Assignee: Kissei Pharmaceutical Co., Ltd., Japan

[21] Appl. No.: 233,487

[22] Filed: Aug. 17, 1988

[30] Foreign Application Priority Data

Aug. 20, 1987 [JP] Japan .............................. 62-207330

[51] Int. Cl.$^5$ .................. C07D 207/28; A61K 31/40; A61K 31/44
[52] U.S. Cl. .................... 514/343; 514/423; 546/281; 548/534; 548/537
[58] Field of Search ............... 546/281; 548/534, 537; 514/343, 423

[56] References Cited

U.S. PATENT DOCUMENTS 2,651,639  9/1953  Angier ................. 548/537
3,051,722  8/1962  Biel ...................... 548/534

FOREIGN PATENT DOCUMENTS 2456634  8/1976  Fed. Rep. of Germany ...... 548/534

Primary Examiner—Mary C. Lee
Assistant Examiner—Mary Sue Howard
Attorney, Agent, or Firm—Depaoli & O'Brien

[57] ABSTRACT

In one embodiment this invention provides novel 2-pyrrolidone-5-carboxylic acid compounds, and pharmaceutically acceptable salts thereof, represented by the formula:

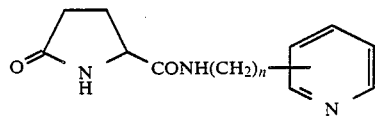

where n is an integer with a value of 1–4. The compounds have application in the treatment of mental disorders such as dementia and amnesis.

7 Claims, No Drawings

2-PYRROLIDONE-5-CARBOXYLIC ACID COMPOUNDS USEFUL FOR THE TREATMENT OF MENTAL DISORDERS

FIELD OF THE INVENTION

The present invention relates to 2-pyrrolidone-5-carboxylic acid compounds which are useful as therapeutic agents. More particularly, the present invention relates to pharmaceutical compositions containing a therapeutically active 2-pyrrolidone-5-carboxylic acid compound, or a pharmaceutically acceptable salt thereof, represented by the general formula:

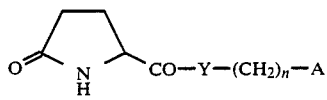

where A is a phenyl, halophenyl or pyridyl group; n is an integer with a value of 1-4; and Y is —O— or —NH—; and to methods for the treatment of mental disorders such as dementia and amnesia by administration of a present invention pharmaceutical composition.

The present invention also relates to novel 2-pyrrolidone-5-carboxylic acid compounds, and pharmaceutically acceptable salts thereof, represented by the general formula:

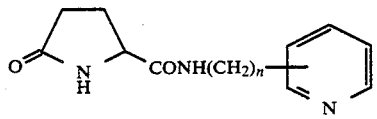

where n is an integer with a value of 1-4.

BACKGROUND OF THE INVENTION

Cerebral vasodilators and cerebral excitometabolic agents are being employed as therapeutical agents for the treatment of diseases such as dementia and amnesia. These agents are effective for the treatment of diseases such as dementia caused by cerebrovascular disorders. However, these agents do not show a sufficient therapeutic effect for the treatment of dementia-type diseases due to causes other than cerebrovascular disorders.

With respect to the present invention, 2-pyrrolidone-5-carboxylic acid compounds of pertinent interest have been published in the technical literature. For example, Chemical Abstracts, Vol. 85, No. 19, 142978d (1976) discloses the compounds represented by the general formula:

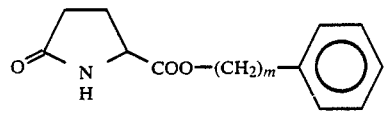

where m is an integer with a value of 1-4. These compounds exhibit a mild antibacterial effect, and are useful as cosmetics such as deodorants and skin conditioners. There is no disclosure in the literature that these compounds have potential application as therapeutical agents for the treatment of mental disorders such as dementia and amnesia.

Chemical Abstracts, Vol. 100, No. 5, 34562h (1984), discloses the compound represented by the formula:

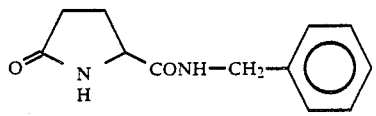

which is useful as an intermediate for the production of antihypertensive agents. There is no disclosure in the publication of any biological activities exhibited by the compound.

Chemical Abstracts, Vol. 80, 82678r (1974), discloses the compound represented by the formula:

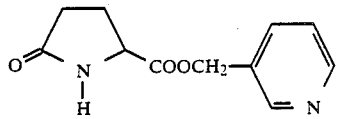

which is illustrated as one of 3-pyridine methanol derivatives having vasodilating activities, and having utility as vasodilators and psychotropic agents. There is no disclosure or suggestion in the publication that the compound might be useful as a therapeutical agent for the treatment of dementia and amnesia.

SUMMARY OF THE INVENTION

An object of this invention is to provide novel 2-pyrrolidone-5-carboxylic acid compounds and pharmaceutically acceptable salts thereof, which are useful as therapeutical agents for the treatment of diseases such as dementia and amnesia.

Another object of this invention is to provide pharmaceutical compositions for the treatment of dementia and amnesia. A further object of this invention is to provide methods for the treatment of diseases such as dementia and amnesia by using a 2-pyrrolidone-5-carboxylic acid compound or a pharmaceutically acceptable salt thereof.

Other objects, features and advantages of the present invention will be apparent from the following description of the invention.

DETAILED DESCRIPTION OF THE INVENTION

The present invention is directed to 2-pyrrolidone-5-carboxylic acid compounds represented by the general formula (I):

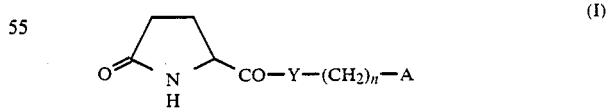

(I)

where A is a phenyl, halophenyl, or pyridyl group; n is an integer with a value of 1-4; Y is —O— or —NH—; and pharmaceutically acceptable salts thereof. This type of 2-pyrrolidone derivative can improve conditions of amnesia induced by electro-convulsive shock (hereinafter referred to as ECS) or by scopolamine injection when administered orally to mice, and thus they are useful as therapeutic agents for the treatment of diseases such as dementia and amnesia.

Of the 2-pyrrolidone-5-carboxylic acid type compounds of the present invention, the derivatives represented by the general formula:

where n is an integer with a value of 1-4, are novel compounds.

The 2-pyrrolidone-5-carboxylic acid compounds (I) of the present invention can be prepared by reacting a compound represented by the formula (II):

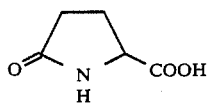

or a reactive functional derivative thereof with a compound represented by the formula (III):

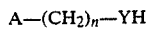

wherein A, n and Y are as previously defined.

The compounds (II) and (III) used as starting materials are commercially available chemicals. They can be obtained also by synthesis methods described in the literature.

The production of the compounds of the general formula (I) of the present invention can be accomplished by conventional procedures, such as using the carboxylic acid compound of formula (II) as a starting material. The synthesis can be conducted in an inert solvent in the presence of a condensing agent such as N,N'-dicyclohexylcarbodiimide.

When a reactive functional derivative of the formula (II) carboxylic acid is used as a starting material to prepare the compounds of the general formula (I) of the present invention, optionally the process can be conducted in the presence of a basic substance in an inert solvent. Illustrative of reactive functional derivatives of the formula (II) carboxylic acid are acid halides, acid anhydrides, mixed acid anhydrides, active esters, and the like.

The 2-pyrrolidone-5-carboxylic acid compounds of the present invention contain an asymmetric carbon atom in the 2-pyrrolidone-5-carboxylic acid moiety, and therefore stereoisomers of the 2-pyrrolidone-5-carboxylic acid compounds of the present invention exist depending upon the configuration of the asymmetric carbon atom. The configurations of substituents on the asymmetric carbon atom may be of R- or S-configuration, and in the practice of the present invention a racemic mixture of S- and R-configurations can be employed. Optically active compounds of the general formula (I) can be prepared by using optically active starting materials.

Of the 2-pyrrolidone-5-carboxylic acid compounds represented by the invention general formula (I), the compounds in which n is 1 and A is a pyridyl group are preferred. The compound N-(2-pyridylmethyl)-2-pyrrolidone-5-carboxamide exhibits a high level of therapeutical activity for the treatment of dementia and amnesia in mammals.

The 2-pyrrolidone-5-carboxylic acid compounds represented by the general formula (I) where A is a pyridyl group can be converted according to conventional methods into pharmaceutically acceptable salts thereof. Examples of such pharmaceutically acceptable salts include pharmaceutically acceptable inorganic or organic acid salts such as hydrochloric acid salt, sulfuric acid salt, p-toluenesulfonic acid salt, acetic acid salt, citric acid salt, tartaric acid salt, succinic acid salt, fumaric acid salt, and the like. These salts also improve conditions of amnesia in mice.

The 2-pyrrolidone-5-carboxylic acid compounds of the general formula (I) can significantly improve conditions of amnesia induced by scopolamine injection or ECS when administered orally to mice at the dose of 1 $\mu$mole/body.

Thus, the 2-pyrrolidone-5-carboxylic acid compounds of the present invention improve conditions of dementia and amnesia, and they are useful as therapeutical agents with a low toxicity for the treatment of diseases such as dementia and amnesia.

The 2-pyrrolidone-5-carboxylic acid compounds of general formula (I) and pharmaceutically acceptable salts thereof can be administered to human or other mammalia by oral, intravenous, intramuscular or intrarectal administration, and for administration they can be formulated into pharmaceutical compositions together with conventional pharmaceutically acceptable carriers or excipients.

The 2-pyrrolidone-5-carboxylic acid compounds and the pharmaceutically acceptable salts of the general formula (I) can be administered in various dosage forms depending upon the intended therapy. Typical dosage forms which can be used are tablets, pills, powders, liquid preparations, suspensions, emulsions, granules, capsules, suppositories, and injectable preparations.

In molding the pharmaceutical compositions into a tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. The tablets, if desired, can be coated into sugar-coated tablets, gelatin-coated tablets, film-coated tablets, or tablets coated with two or more layers.

When a pharmaceutical composition is formulated into an injectable preparation, it is preferred that the resulting injectable solution and suspension are sterilized and rendered isotonic with respect to blood. In making the pharmaceutical composition in a form of solution or suspension, any diluents customarily used in the art can be employed. Examples of suitable diluents include water, ethyl alcohol, propylene glycol, polyoxyethylene sorbitol, and sorbitan esters. Sodium chloride, glucose or glycerol may be incorporated into such a liquid preparation in an amount sufficient to prepare an isotonic solution. The therapeutic agent may further contain ordinary dissolving aids, buffers, pain-alleviating agents, and preservatives, and optionally, coloring agents fragrances, flavors, sweeteners, and other pharmacologically active agents which are known in the art.

The dosage of the 2-pyrrolidone-5-carboxylic acid derivatives of the present invention may be in the range from about 50 mg to 1000 mg for adult human by oral administration per day, or from about 1 mg to 500 mg for adult human by parenteral administration per day in multiple doses depending upon the type of disease, the severity of condition to be treated, and the like.

The present invention is further illustrated in more detail by way of the following examples. The reported melting points of the products are uncorrected.

EXAMPLE 1 p-Chlorobenzyl 2-pyrrolidone-5-carboxylate
(Compound 1)

To a solution of 7.38 g of 2-pyrrolidone-5carboxylic acid in 250 ml of N,N-dimethylformamide was added 2.14 g of a 60% sodium hydride (a dispersion in oil) which was washed with dry benzene, and the mixture was stirred for 1 hour at room temperature. To the mixture was added a solution of 7.67 g of p-chlorobenzylchloride in 50 ml of N,N-dimethylformamide, and then the mixture was stirred overnight at 50° C. The reaction mixture was evaporated under reduced pressure, and the residue was dissolved in chloroform. The organic layer was washed successively with an aqueous sodium bicarbonate solution and water, dried over anhydrous magnesium sulfate, and evaporated under reduced pressure. The residue was recrystallized from benzene to obtain 10.2 g of p-chlorobenzyl 2-pyrrolidone-5-carboxylate (yield 84.4%)

melting point: 119°–120° C.

IR (KBr): $\nu co$ 1740, 1680 cm$^{-1}$.

NMR (CDCl$_3$) $\delta$: 2.05–2.62(m, 4H), 4.18–4.38(m, 1H), 5.12(s, 2H), 7.07(br-s, 1H), 7.16–7.40(m, 4H).

elemental analysis as C$_{12}$H$_{12}$NO$_3$Cl.

|  | C % | H % | N % |
| --- | --- | --- | --- |
| Calcd. | 56.82 | 4.77 | 5.52 |
| Found | 57.02 | 4.84 | 5.52 |

EXAMPLE 2

2-Pyridylmethyl 2-pyrrolidone-5-carboxylate
(Compound 2)

To 90 ml of thionyl chloride was added dropwise 23.5 g of 2-pyrrolidone-5-carboxylic acid with stirring under ice-cooling, and the mixture was stirred for 30 minutes at 40°–50° C. After cooling of the reaction mixture, 200 ml of dry diethyl ether was added to the reaction mixture, and the reaction mixture was allowed to stand overnight in a freezing box. Precipitated crystals were collected by filtration, washed with dry diethyl ether, and dried in a desiccator to obtain 27 g of 2-pyrrolidone-5-carbonyl chloride. The obtained acid chloride was dissolved in 500 ml of dry chloroform, and to the solution were added 13.5 g of 2-pyridylmethanol with stirring at room temperature, and then the reaction mixture was heated under refluxing. After completion of the reaction, to the reaction mixture was added an aqueous sodium bicarbonate solution to make the solution basic at pH 9, and the reaction mixture was extracted with chloroform. The organic layer was washed with water, dried over anhydrous magnesium sulfate, and evaporated under reduced pressure. The residue was recrystallized from benzene to obtain 16.2 g of 2-pyridylmethyl 2-pyrrolidone-5-carboxylate. (yield 60.0%)

melting point: 130°–131° C.

IR (KBr): $\nu co$ 1740, 1695 cm$^{-1}$.

NMR (CDCl$_3$) $\delta$: 2.16–2.82(m, 4H), 4.29–4.51(m, 1H), 5.31 s, 2H), 7.11(br-s, 1H), 7.20–7.87(m,3H), 8.55–8.69(m,1H)

Elemental analysis as C$_{11}$H$_{12}$N$_2$O$_3$.

|  | C % | H % | N % |
| --- | --- | --- | --- |
| Calcd. | 59.99 | 5.49 | 12.72 |
| Found | 59.96 | 5.47 | 12.80 |

EXAMPLE 3

The following compounds can be prepared according to the same procedure as that described in Example 2.

3-Pyridylmethyl 2-pyrrolidone-5-carboxylate
(Compound 3)

melting point: 97°–101° C. (benzene-n-hexane)

IR (KBr): $\nu co$ 1745, 1690 cm$^{-1}$.

NMR (CDCl$_3$). $\delta$: 2.04–2.67(m, 4H), 4.24–4.44(m, 1H), 5.22(s, 2H), 7.22–7.44(m, 2H), 7.64–7.82(m, 1H), 8.55–8.71(m, 2H).

Elemental analysis as C$_{11}$H$_{12}$N$_2$O$_3$.

|  | C % | H % | N % |
| --- | --- | --- | --- |
| Calcd. | 59.99 | 5.49 | 12.72 |
| Found | 60.21 | 5.57 | 12.68 |

4-Pyridylmethyl 2-pyrrolidone-5-carboxylate
(Compound 4)

melting point: 85°–89° C. (benzene-diethyl ether).

IR (KBr): $\nu co$ 1745, 1700 cm$^{-1}$.

NMR (CDCl$_3$) $\delta$: 2.11–2.66(m, 4H), 4.26–4.47(m, 1H), 5.19(s, 2H), 7.18–7.38(m, 2H), 7.58(br-s, 1H), 8.53–8.67(m, 2H).

Elemental analysis as C$_{11}$H$_{12}$N$_2$O$_3$.

|  | C % | H % | N % |
| --- | --- | --- | --- |
| Calcd. | 59.99 | 5.49 | 12.72 |
| Found | 59.77 | 5.46 | 12.76 |

2-(2-Pyridyl)ethyl 2-pyrrolidone-5-carboxylate
(Compound 5)

melting point: 93°–94.5° C. (acetone-diethyl ether)

IR (KBr): $\nu co$ 1730, 1690 cm$^{-1}$.

NMR (CDCl$_3$). $\delta$:2.04–2.55(m, 4H), 3.16(t, 2H), 4.11–4.29(m, 1H), 4.56(t, 2H), 5.84(br-s, 1H), 7.04–7.20(m, 2H), 7.51–7.73(m, 1H), 8.44–8.55(m, 1H).

Elemental analysis as C$_{12}$H$_{14}$N$_2$O$_3$.

|  | C % | H % | N % |
| --- | --- | --- | --- |
| Calcd. | 61.52 | 6.02 | 11.96 |
| Found | 61.52 | 6.11 | 11.85 |

3-(2-Pyridyl)propyl 2-pyrrolidone-5-carboxylate
(Compound 6)

melting point: 47°–51° C. (acetone-diethyl ether).

IR (KBr): $\nu co$ 1735, 1700 cm$^{-1}$.

NMR (CDCl$_3$) $\delta$: 1.98–2.62(m, 6H), 2.78–3.00(m, 2H), 4.16–4.36(m, 3H), 6.91–7.22(m, 3H), 7.51–7.73(m, 1H), 8.47–8.62(m, 1H).

Elemental analysis as C$_{13}$H$_{16}$N$_2$O$_3$.

|  | C % | H % | N % |
|---|---|---|---|
| Calcd. | 62.89 | 6.50 | 11.28 |
| Found | 62.96 | 6.53 | 11.38 |

EXAMPLE 4

N-(2-Pyridylmethyl)-2-pyrrolidone-5-carboxamide (Compound 7)

To a solution of 8.6 g of 2-aminomethylpyridine in ml of dry chloroform were added 16.2 g of triethylamine, and to the mixture were added 12 g of 2-pyrrolidone-5-carbonylchloride in small portions with stirring and ice-cooling.

After stirring the reaction mixture overnight at room temperature, the reaction mixture was evaporated under reduced pressure. The residue was dissolved in water, and to the solution was added an aqueous sodium bicarbonate solution to make the solution basic at pH 8. The reaction mixture was extracted with chloroform, and the organic layer was dried over anhydrous magnesium sulfate, and evaporated under reduced pressure. The residue was triturated with diethyl ether. Precipitated crystals were collected by filtration and recrystallized from acetone to obtain 8.7 g of N-(2-pyridylmethyl)-2-pyrrolidone-5-carboxamide. (yield 49.7%)

melting point: 134°–135° C.

IR (KBr): $\nu_{co}$ 1690, 1655 cm$^{-1}$.

NMR (CDCl$_3$) δ: 2.06–2.73(m, 4H), 4.15–4.38(m, 1H), 4.54(d, 2H), 7.02–8.44(m, 6H).

Elemental analysis as $C_{11}H_{13}N_2O_3$.

|  | C % | H % | N % |
|---|---|---|---|
| Calcd. | 60.26 | 5.89 | 19.15 |
| Found | 60.12 | 5.89 | 19.13 |

EXAMPLE 5

Anti-amnesic effect

Anti-amnesic effects of the compounds were determined by the following tests.

Male mice of dd-strain, weighing 23–30 g, were employed for the experiment, and the test compounds were freshly dissolved in saline and administered orally at a dose of 1 μmole/mouse.

(1) One trial passive avoidance task by step-through test

A shuttle box composed of a light (7 cm high, 9 cm wide and 15 cm depth) and a dark (12 cm high, 13 cm wide and 15 cm depth) box; the former was lighted using 15W-white light fluorescent bar lamp placed at the position of 40 cm from the floor and in the latter the stainless steel floor grids 2.5 mm in diameter were placed at intervals of 4 mm in order to give a foot shock. Both boxes were connected with a gate 3 cm in diameter.

As the training trial, each animal was placed in the light box and a foot shock (35V) was delivered through the floor grid immediately after the animal entered into the dark box, accordingly the animal learned a punishment for the entrance.

The intensities of the shocks were 35V and 40V on the experiment for acquisition of learning and on the experiment for observation of effect to the amnesia induced by ECS, respectively.

Twenty-four hr after the training trial, the animal was placed again in the light box and step-through (ST) latency, time spent until the animal entered the dark box, was measured.

Application of transpinnal electro-convulsive shock (ECS, 100V for 0.4 sec) produced an amnesic state in the animal, and in this case the animal received 40V of foot shock at the training trial.

A test compound was administered orally 1 hr before the training trial.

The ST-latency on the test trial was measured up to 300 and 600 sec for control and amnesic group, respectively.

[Test compounds]

p-Chlorobenzyl 2-pyrrolidone-5-carboxylate (compound 1)

N-(2-Pyridylmethyl)-2-pyrrolidone-5-carboxamide (compound 7)

[Results]

The ST-latency in ECS-induced amnesic mice was shortened significantly compared to that in the control group.

The compound 1 prolonged the ST-latency in ECS-induced amnesic mice significantly and the compound 7 recovered the shortened ST-latency to the control level.

(2) One trial passive avoidance task by Step-down method

An apparatus (25L×25W×25H cm) with the grid floor to give a foot shock, and a platform (7L×7W×3H cm) placed in the corner was used for avoidance experiment.

As the training trial, an animal was placed on the platform and a foot shock was given through the floor grid when the animal stepped down to the floor, and the animal immediately returned to the home cage.

Twenty-four hr after the training trial, the animal was placed again on the platform and step-down (SD) latency, time spent until the animal stepped down to the floor, was measured.

Test compounds were administered 1 hr before the training trial. Scopolamine, 1 mg/kg, was intraperitoneally injected to induce amnesic state 30 min prior to the training trial.

[Test compounds]

p-Chlorobenzyl-2-pyrrolidone-5-carboxylate (compound 1)

N-(2-Pyridylmethyl)-2-pyrrolidone-5-carboxamide (compound 7)

[Results]

The SD-latency was shortened in scopolamine-induced amnesic animals compared to that in the control group, and compound 7 recovered the shortened SD-latency to the control level.

EXAMPLE 6

Acute toxicity

The test compounds were administered to male mice of SCL-ICR-strain, 7 weeks age, at several dosage (single shot) and LD$_{50}$, 50% lethal dose, was estimated from the number of lethal mice at 1 week past to the administration.

[Results]

| compound No. | LD$_{50}$ (mg/kg) |
|---|---|
| 1 | >2592 |
| 2 | 1538 |
| 3 | >2592 |
| 4 | >2592 |
| 5 | >2592 |
| 6 | <1250 |
| 7 | >2592 |

EXAMPLE 7

Formulate example

The following pharmaceutical compositions were formulated.

(A) Powders

The formula for 1000 powders:

| Compound 1 | 25 g |
|---|---|
| Lactose | 975 g |
| | 1000 g |

Above substances were admixed well to make powders.

(B) Powders

The formula for 1000 powders:

| Compound 1 | 5 g |
|---|---|
| Lactose | 495 g |
| | 500 g |

Above substances were admixed well to make powders.

(C) Tablets

The formula for 1000 tablets:

| Compound 1 | 25 g |
|---|---|
| Lactose | 140 g |
| 6% HPC-Lactose | 110 g |
| Potate Starch | 20 g |
| Talc Stearate | 5 g |
| | 300 g |

Above substances were admixed well and the mixture was formulated to b 1000 tablets with a tablet machine.

(D) Tablets

The formula for 1000 tablets:

| Compound 1 | 5 g |
|---|---|
| Lactose | 150 g |
| 6% HPC-Lactose | 120 g |
| Potate Starch | 20 g |
| Talc Stearate | 5 g |
| | 300 g |

Above substances were admixed well and the mixture was formulated to b 1000 tablets with a tablet machine.

(E) Capsules

The formula for 1000 capsules:

| Compound 1 | 25 g |
|---|---|
| Lactose | 220 g |
| Potate Starch | 50 g |
| Talc Stearate | 5 g |
| | 300 g |

Above substances were admixed well and the mixture was filled to 1000 hard capsules in an equal portion to make capsules.

(F) Capsules

The formula for 1000 capsules:

| Compound 1 | 5 g |
|---|---|
| Lactose | 235 g |
| Potato Starch | 55 g |
| Talc Stearate | 5 g |
| | 300 g |

Above substances were admixed well and the mixture was filled to 1000 hard capsules in an equal portion to make capsules.

We claim:

1. A method for the treatment of dementia or amnesia which comprises administering a prescribed dosage of a pharmaceutical composition containing as an active ingredient a 2-pyrrolidone-5-carboxylic acid compound represented by the general formula:

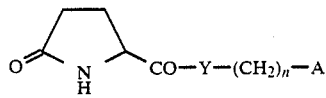

where A is a phenyl, halophenyl or pyridyl group; n is an integer with a value of 1-4; Y is —O— or —NH—; or a pharmaceutically acceptable salt thereof.

2. A method of treatment in accordance with claim 1 wherein the active ingredient is a 2-pyrrolidone-5-carboxylic acid compound represented by the general formula:

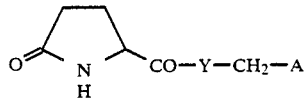

wherein A and Y are as previously defined; or a pharmaceutically acceptable salt thereof.

3. A method of treatment in accordance with claim 1 wherein the active ingredient is a 2-pyrrolidone-5-carboxylic acid compound represented by the formula:

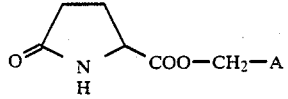

wherein A is as previously defined; or a pharmaceutically acceptable salt thereof.

4. A method of treatment in accordance with claim 1 wherein the active ingredient is a 2-pyrrolidone-5-carboxylic acid compound represented by the general formula:

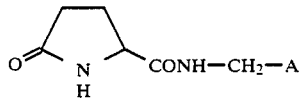

wherein A is as previously defined; or a pharmaceutically acceptable salt thereof.

5. A method of treatment in accordance with claim 1 wherein the prescribed dosage of pharmaceutical composition is in the range from about 50 mg to 1000 mg for an adult human by oral administration per day, or from about 1 mg to 500 mg for an adult human by parenteral administration per day.

6. A method for the treatment of dementia or amnesia in a human patient which comprises administering a prescribed dosage of a pharmaceutical composition containing N-(2-pyridylmethyl)-2-pyrrolidone-5-carboxamide as an active ingredient, or a pharmaceutically acceptable salt thereof.

7. p-Chlorobenzyl 2-pyrrolidone-5-carboxylate.

* * * * *

UNITED STATES PATENT AND TRADEMARK OFFICE
CERTIFICATE OF CORRECTION

PATENT NO.   : 4,933,354
DATED        : June 12, 1990
INVENTOR(S)  : Ikeguchi et al It is certified that error appears in the above-identified patent and that said Letters Patent is hereby corrected as shown below:

First page of patent, "Inventors:" section, "Seiichi Ikeguchi" is from --Nagano-ken-- not "Kisofukushima".

In the Abstract, last line, "amnesis" should be --amnesia--.

Col. 7, line 11, "in ml of" should be --in 150 ml of--.

Signed and Sealed this

Third Day of September, 1991

Attest:

HARRY F. MANBECK, JR.

Attesting Officer

Commissioner of Patents and Trademarks